United States Patent
Stchur et al.

(10) Patent No.: US 11,666,347 B2
(45) Date of Patent: Jun. 6, 2023

(54) SURGICAL RETRACTOR AND RESECTION GUIDE

(71) Applicant: Sure Orthopedics LLC, Sarasota, FL (US)

(72) Inventors: Robert Patrick Stchur, Punta Gorda, FL (US); John D. Kuczynski, Sarasota, FL (US)

(73) Assignee: Sure Orthopedics LLC, Sarasota, FL (US)

(*) Notice: Subject to any disclaimer, the term of this patent is extended or adjusted under 35 U.S.C. 154(b) by 314 days.

(21) Appl. No.: 17/098,260

(22) Filed: Nov. 13, 2020

(65) Prior Publication Data

US 2021/0145462 A1  May 20, 2021

Related U.S. Application Data

(60) Provisional application No. 62/974,106, filed on Nov. 14, 2019.

(51) Int. Cl.

| A61B 17/17 | (2006.01) |
|---|---|
| A61B 17/02 | (2006.01) |
| A61B 17/88 | (2006.01) |
| A61B 17/16 | (2006.01) |
| A61B 17/00 | (2006.01) |
| A61B 17/90 | (2006.01) |

(52) U.S. Cl.
CPC ...... *A61B 17/1778* (2016.11); *A61B 17/0206* (2013.01); *A61B 17/1684* (2013.01); *A61B 17/8897* (2013.01); *A61B 17/90* (2021.08); *A61B 2017/00477* (2013.01)

(58) Field of Classification Search
CPC .............. A61B 17/0206; A61B 17/025; A61B 17/8897; A61B 17/90; A61B 2017/00477; A61B 2090/067; A61B 17/1684; A61B 17/1778; A61B 17/15
See application file for complete search history.

(56) References Cited

U.S. PATENT DOCUMENTS

2015/0359576 A1* 12/2015 Ponce ................ A61B 17/8061
606/280

OTHER PUBLICATIONS

"Comprehensive Total Shoulder System: Surgical Technique", Zimmer Biomet, 2018, 56 pages.
"ReUnion TSA Total Shoulder Arthroplasty System," stryker, 2019, 118 pages.

* cited by examiner

*Primary Examiner* — Samuel S Hanna
(74) *Attorney, Agent, or Firm* — Kim IP Law Group LLC

(57) ABSTRACT

A surgical instrumentation system for a shoulder arthroplasty that includes a retractor that includes a curved section structured to wrap around and substantially engage a posterior portion of a humeral head, an alignment guide extending from the retractor. The alignment guide includes a primary alignment shaft and a resection guide attachable to the retractor, the resection guide including a guide surface for guiding a cutting tool.

8 Claims, 13 Drawing Sheets

SURGICAL RETRACTOR AND RESECTION GUIDE

CROSS-REFERENCE TO RELATED APPLICATIONS

This application claims the benefit of U.S. Provisional Application No. 62/974,106 filed Nov. 14, 2019, entitled "Retractor Based Alignment Guides for Shoulder Arthroplasty Surgery" the entire disclosure of which is incorporated by reference herein in its entirety for all purposes.

BACKGROUND OF THE DISCLOSURE

Exemplary embodiments of the subject disclosure relate generally to a surgical retractor and humeral resection guide that can be used, for example, in a shoulder arthroplasty procedure (e.g., a reverse shoulder arthroplasty).

Surgical retractors are used to obtain and maintain access to the anatomy being operated on during a surgical procedure. For most surgeries, several layers of tissue must be dissected through and moved aside (retracted) in order to access the anatomy to perform the operative procedure. It may be necessary to retract soft tissues, such as skin, muscle, fat, and internal organs or bony tissue, or both. While dissecting to reach the surgical site, the surgeon must also avoid damaging certain tissues, such as neural or vascular structures. A retractor system should allow the surgical team to access the surgical site by pushing the tissues aside and holding them in place while doing as little damage as possible to those tissues and also protecting particularly sensitive tissues such as nerves or vascular structures.

Space is an issue when performing an operation, such as a reverse shoulder arthroplasty (RSA). Access to the surgical site is limited by soft tissue, bone and also neural and vascular structures that must be protected and avoided. Retractors must be placed and held to access the surgical site, and often an alignment and/or resection guide must then be placed to perform the resection or drilling. In some cases the retractors can interfere with other instruments. It is also necessary to control the retractor and the alignment/resection instrument separately, sometimes requiring two or more people to hold the retractor(s) and control the instrument being used. Accordingly, there remains a need for improved systems for providing retraction and resection of anatomical parts during operative procedures.

SUMMARY OF THE DISCLOSURE

In accordance with an exemplary embodiment, the subject disclosure provides a surgical instrumentation system for a shoulder arthroplasty that includes a retractor, an alignment guide and a resection guide. The retractor includes a curved section structured to wrap around and substantially engage a posterior portion of a humeral head. The alignment guide extends from the retractor and includes a primary alignment shaft. In certain exemplary embodiments, the primary alignment shaft extends substantially transverse to a longitudinal axis of the retractor. The resection guide is attachable to the retractor, and includes a guide surface for guiding a cutting tool. In exemplary embodiments, the guide surface can be a captured guide surface or an open guide surface, and the retractor and the alignment guide can be of unitary construction.

In exemplary embodiments of the subject disclosure, the curved section comprises an arc from about 140 to 210 degrees. The retractor can further include a shaft extending from the curved section, the resection guide structured to engage the shaft and be movable in a longitudinal direction of the shaft. The resection guide can, in exemplary embodiments, include a guide aperture for receiving a shaft of the retractor.

In accordance with another exemplary embodiment, the subject disclosure provides a surgical instrument for a shoulder arthroplasty that includes a retractor, an alignment guide extending from the retractor, a humerus alignment shaft extending from the alignment guide and a resection guide attachable to retractor, the resection guide including a guide surface for guiding a cutting tool. In exemplary embodiments, the retractor includes a curved section structured to wrap around and substantially engage a posterior portion of a humeral head, and a shaft extending from the curved section defining a plane. The alignment guide can include a plurality of forearm alignment shafts, each forearm alignment shaft extending obliquely from a central location of the shaft.

In exemplary embodiments, the alignment guide includes a first forearm alignment shaft, a second forearm alignment shaft and a third forearm alignment shaft, each extending from the central location. For example, the first forearm alignment shaft can extend about 140 to about 145 degrees, the second forearm alignment shaft can extend about 152 to about 157 degrees, and the third forearm alignment shaft can extend about 165 to about 169 degrees, each with respect to the plane.

In other exemplary embodiments, the alignment guide further includes a secondary humerus alignment shaft extending from alignment guide. The alignment guide can extend from the shaft via an orthogonal segment disposed between the shaft and the alignment guide. The alignment guide, humerus alignment shaft, and resection guide can be of unitary construction.

In accordance with yet another exemplary embodiment, the subject disclosure provides a surgical instrumentation system for a shoulder arthroplasty that includes a retractor, a resection guide attachable to the retractor including a guide surface for guiding a cutting tool, and an alignment guide attachable to the retractor. In exemplary embodiments, the retractor includes a curved section structured to wrap around and substantially engage a posterior portion of a humeral head, and a shaft extending from the curved section. In exemplary embodiments, the alignment guide includes a plurality of through holes for receiving a fixation rod therein.

In certain exemplary embodiments, the shaft of the retractor includes a planar side and a curved side opposite the planar side. The resection guide can include a guide aperture for matingly receiving the shaft of the retractor, the guide aperture including a planar side and a curved side opposite the planar side. Alternatively, or in addition, the resection guide can include one or more through holes for receiving a fixation rod therein. In exemplary embodiments, the planar side of the guide aperture is substantially perpendicular to a longitudinal plane defined by the guide surface.

In certain exemplary embodiments, the alignment guide includes a first alignment aperture for matingly receiving the shaft of the retractor. The alignment guide further includes a second alignment aperture spaced from the first alignment aperture. The first and second alignment apertures each includes a planar side and a curved side opposite the planar side. The planar side can be angled relative to a longitudinal axis of the alignment shaft about 30 to 75 degrees.

BRIEF DESCRIPTION OF THE SEVERAL VIEWS OF THE DRAWINGS

The following detailed description of the exemplary embodiments of the subject disclosure will be better understood when read in conjunction with the appended drawings. For the purpose of illustrating the present disclosure, there is shown in the drawings exemplary embodiments. It should be understood, however, that the subject application is not limited to the precise arrangements and instrumentalities shown.

DETAILED DESCRIPTION OF THE DISCLOSURE

Figure 1:
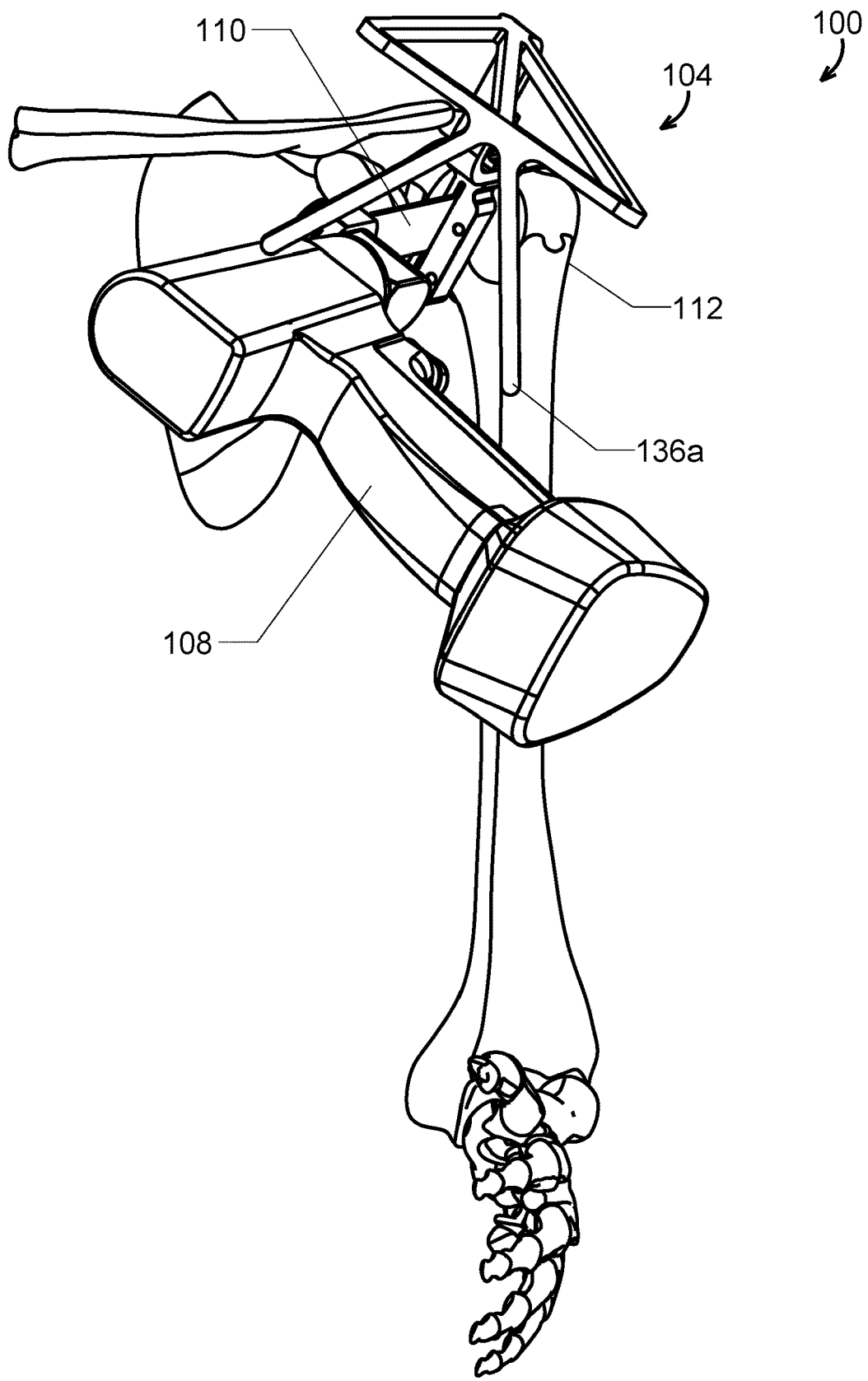
FIG. 1 is a perspective view of a surgical instrumentation system in accordance with an exemplary embodiment of the subject disclosure.
Figure 2:
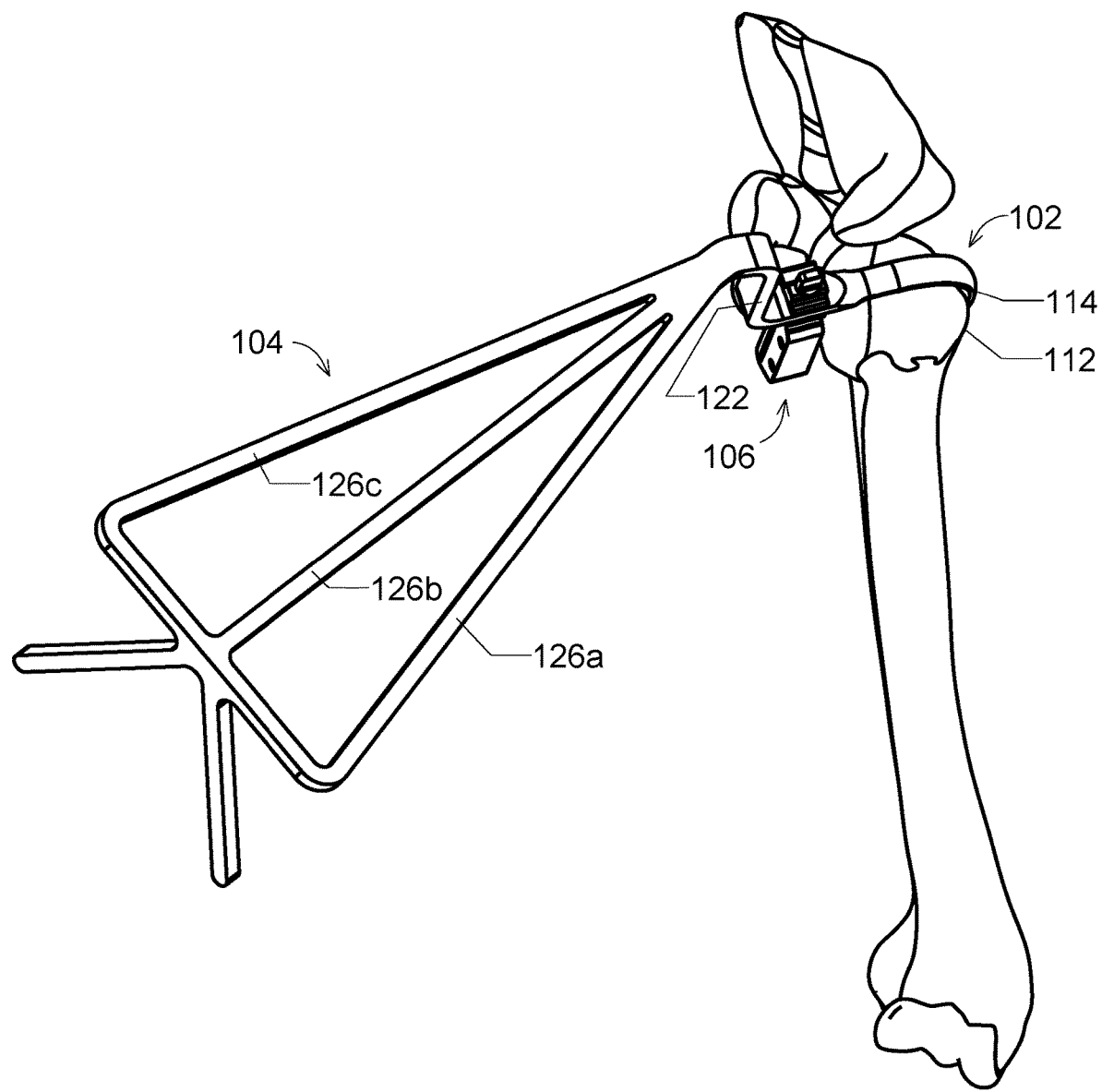
FIG. 2 is another perspective view of the surgical instrumentation system of FIG. 1.

Reference will now be made in detail to the exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

As used herein, the term "adjacent" refers to being near or adjoining. Adjacent components (which can be integral or separate) can be spaced apart from one another, or can be in actual or direct contact with one another (i.e., directly adjacent).

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Referring now to the drawings, FIGS. 1-7 disclose a surgical instrumentation system 100 for a shoulder arthroplasty (e.g., a reverse shoulder arthroplasty). In this exemplary embodiment, the system 100 includes a retractor 102, an alignment guide 104, and a resection guide 106 to guide, e.g., a saw 108 powering a cutting tool 110, in order to resection a humeral head 112.

Figure 3:
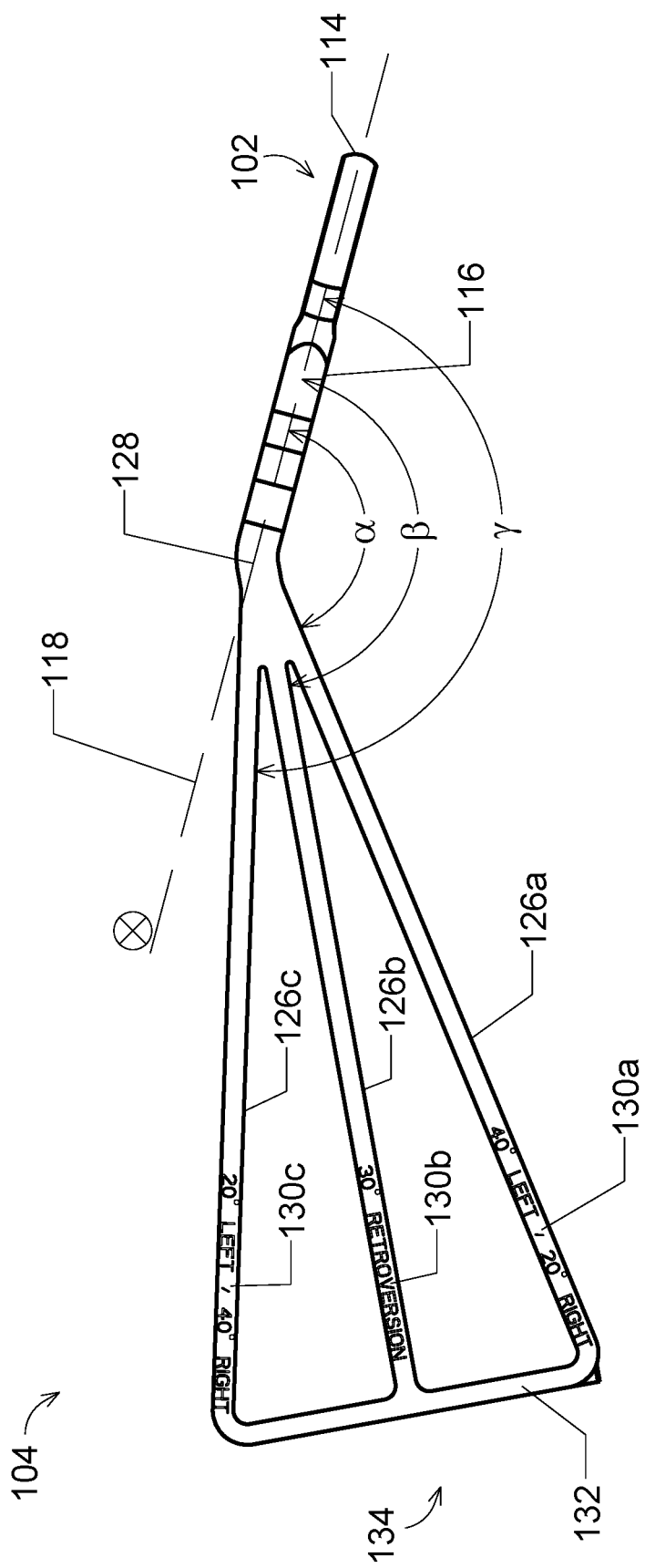
FIG. 3 is a plan view of a retractor of the surgical instrumentation system of FIG. 1.
Figure 4:
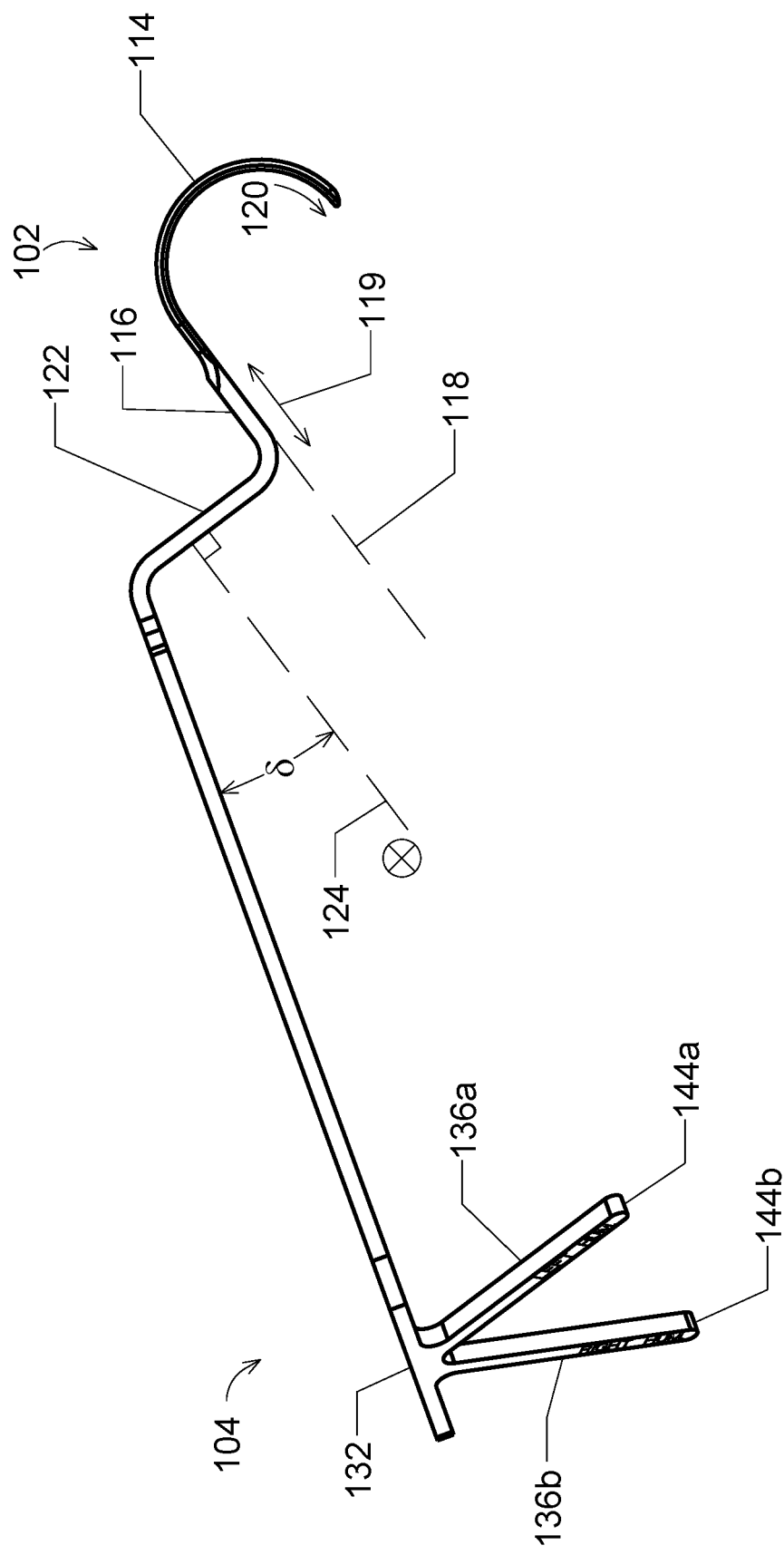
FIG. 4 is a side view of the retractor of FIG. 3.

The retractor 102 (as best shown in FIG. 4) includes a curved section or curved end 114 structured to wrap around and substantially engage a posterior portion of the humeral head 112. The retractor further includes a shaft 116 extending from the curved section 114 that defines a plane 118 that extends into the page or shown in FIG. 3. The shaft 116 extends in a longitudinal direction 119 from a proximal end of the curved section. The curved section defines an arc (e.g., a circular arc) 120 that, in this exemplary embodiment, can range from about 140 degrees to about 210 degrees, including 135, 145, 150, 160, 180, 190, 200, 205, and 215 degrees. Alternatively, other arc shapes and dimensions can be employed to engage the posterior portion of the humeral head 112, including, for example, a plurality of linear segments, or shapes having multiple radius of curvatures. The curved section extends substantially along the plane 118.

The shaft 116 in this exemplary embodiment is rectangularly shaped and is sized to engage the resection guide 106 (e.g., sized to be received by a resection guide aperture and/or fastener). Alternatively, other shaft sizes and shapes can be employed, such as, for example, a rounded or half-rounded shaft. The shaft 116 extends a longitudinal length along plane 118 sufficient to allow room for the resection guide 106 to be adjusted so as to allow direct contact with the humeral head 112. The retractor 102 further includes an orthogonal segment 122 extending, e.g., superiorly from the shaft 116 (as shown in FIG. 4) and defining an orthogonal plane 124 (extending into the page as shown in FIG. 4) orthogonal to plane 118.

With reference to FIG. 4, the alignment guide 104 extends from the retractor 102, e.g. extending obliquely from the orthogonal segment 122 of the retractor at an angle δ from the orthogonal plane 124 that, in certain exemplary embodiments, can range from about 5 degrees to about 30 degrees (e.g., about 10, 15, 17, 20, 25 degrees). In this exemplary embodiment, the alignment guide 104 and the retractor 102 are of unitary construction, though they can alternatively be provided as separate components that can be linked or otherwise connected.

The alignment guide 104 incudes a plurality (e.g., three) forearm or primary alignment shafts 126a, 126b, 126c extending from a central location 128 of the orthogonal segment, as best shown in FIG. 3. In this exemplary embodiment, a first forearm alignment shaft 126a extends at a first angle, α, of about 140 to about 145 degrees (e.g., about 143 degrees), the second forearm alignment shaft 126b extends at a second angle, β, of about 152 to about 157 degrees (e.g., about 155 degrees), and the third forearm alignment shaft 126c extends at a third angle, γ, of about 165 to about 169 degrees (e.g., about 167 degrees), each with respect to the plane 118.

Each of the forearm alignment shafts 126a-c can include, e.g., on its superior-facing surface, an indicia 130a-c that indicates an approximate degree of retroversion that—when the respective forearm alignment shaft 126 is aligned with the subject's forearm—the humeral resection will yield. As this exemplary embodiment can be used for right and left humeral resections, this indicia 130 can be provided to display, e.g., reversion angle information for both left and right humeral resections.

In this exemplary embodiment, the second (middle) forearm alignment shaft 126b will provide approximately 30 degrees of retroversion when aligned with the right or left forearm. The first alignment shaft 126a will provide approximately 40 degrees of retroversion when aligned with the left forearm and 20 degrees of retroversion when aligned with the right forearm and the third alignment shaft will provide approximately 20 degrees of retroversion when aligned with the left forearm and 40 degrees of retroversion when aligned with the right forearm. The alignment guide 104 is dimensioned to provide these resections, and the indicia 130 conveys this information to a surgeon. In alternative embodiments, the alignment guide 104 can be dimensioned to provide other degrees of retroversion and/or additional alignment guides can be provided (e.g., 2, 4, 5, 6 or 7) alignment guides extending from central location 128) to offer additional degrees of retroversion upon alignment with the subject's forearm.

Figure 5:
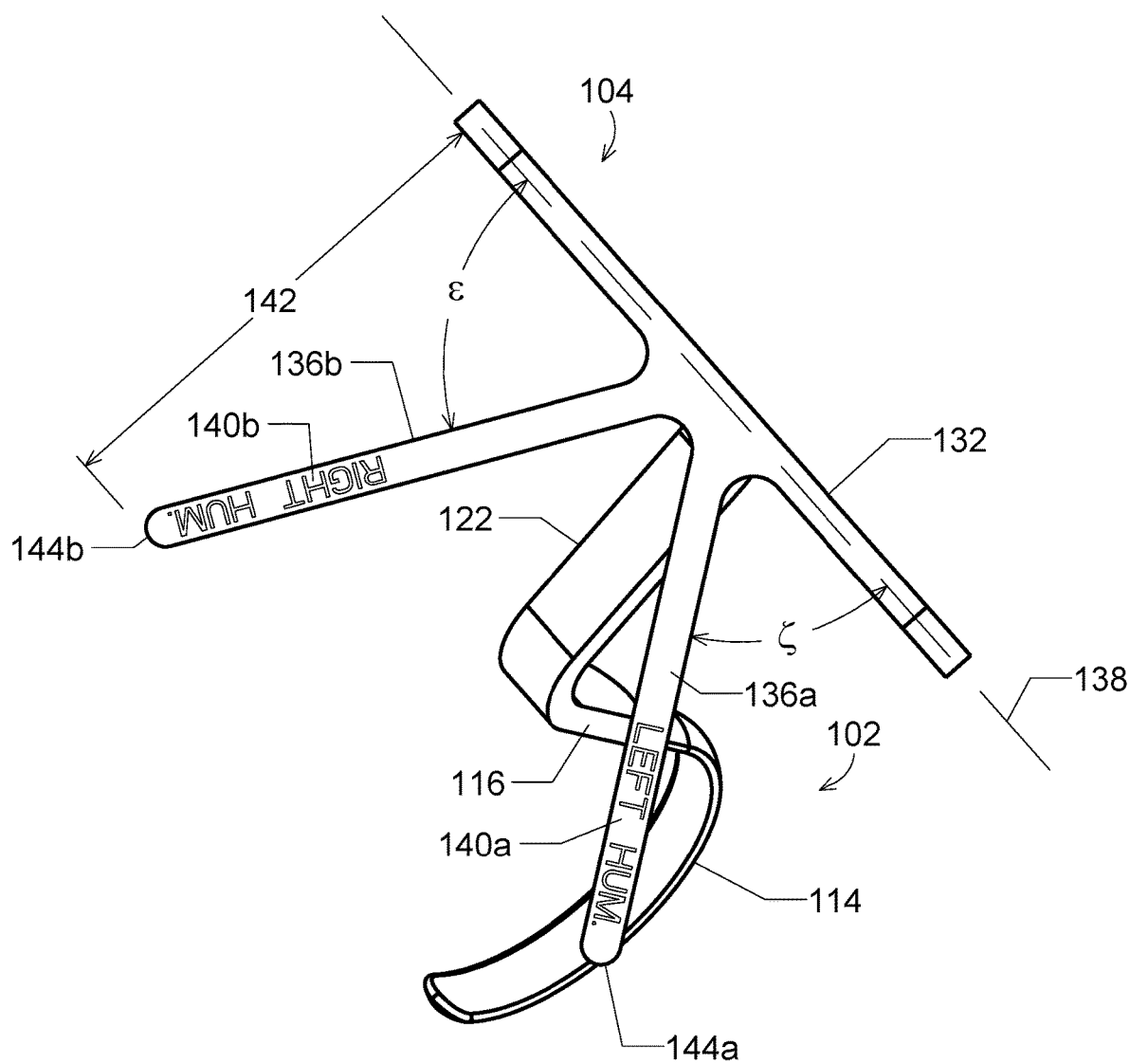
FIG. 5 is a front view of the retractor of FIG. 3.

The forearm alignment shafts 126a-c terminate along a proximal segment 132 that forms a proximal end 134 of the alignment guide 104, and also defines a longitudinal plane 138 (extending into the page, as shown in FIG. 5). A pair of secondary humerus alignment shafts, 136a, 136b, extend from the proximal segment 132, as shown best in FIG. 5, respectively intended to be aligned with the right humerus (when performing a right humerus resection) or the left humerus (when performing a left humerus resection).

In this exemplary embodiment, the left secondary humerus alignment shaft 136a extends at a first angle, ζ, relative to plane 138 that can range from about 45 degrees to about 65 degrees (e.g., 40, 50, 54, 55, 60, and 70 degrees). The right secondary humerus alignment shaft 136b extends at a second angle, ε, that is different from ζ, and can range, for example, from about 55 to about 75 degrees (e.g., 50, 60, 63, 64, 65, 70, 80 degrees). Owing to the geometry and offset angles employed in this exemplary embodiment, the angles ζ and ε are different, yet a single surgical instrumentation system 100 is used for both right and left resections. Each secondary humerus alignment shaft respectively bears a second indicia 140 that can, for example, indicate whether it is to be aligned with the right humerus (140b for right humerus resections) or the left humerus (140a for left humerus resections).

In this exemplary embodiment, each secondary humerus alignment shaft 136a, 136b extends a length 142 (orthogonal to plane 138) of about 70 to 90 mm (e.g. 75, 77, 80, and 85 mm) from the proximal segment 132, as shown in FIG. 5, although other dimensioning can be provided in alternative embodiments. The tips 144a,b of the secondary humerus shafts in this exemplary embodiment are rounded, although other configurations can also be provided.

Figure 6:
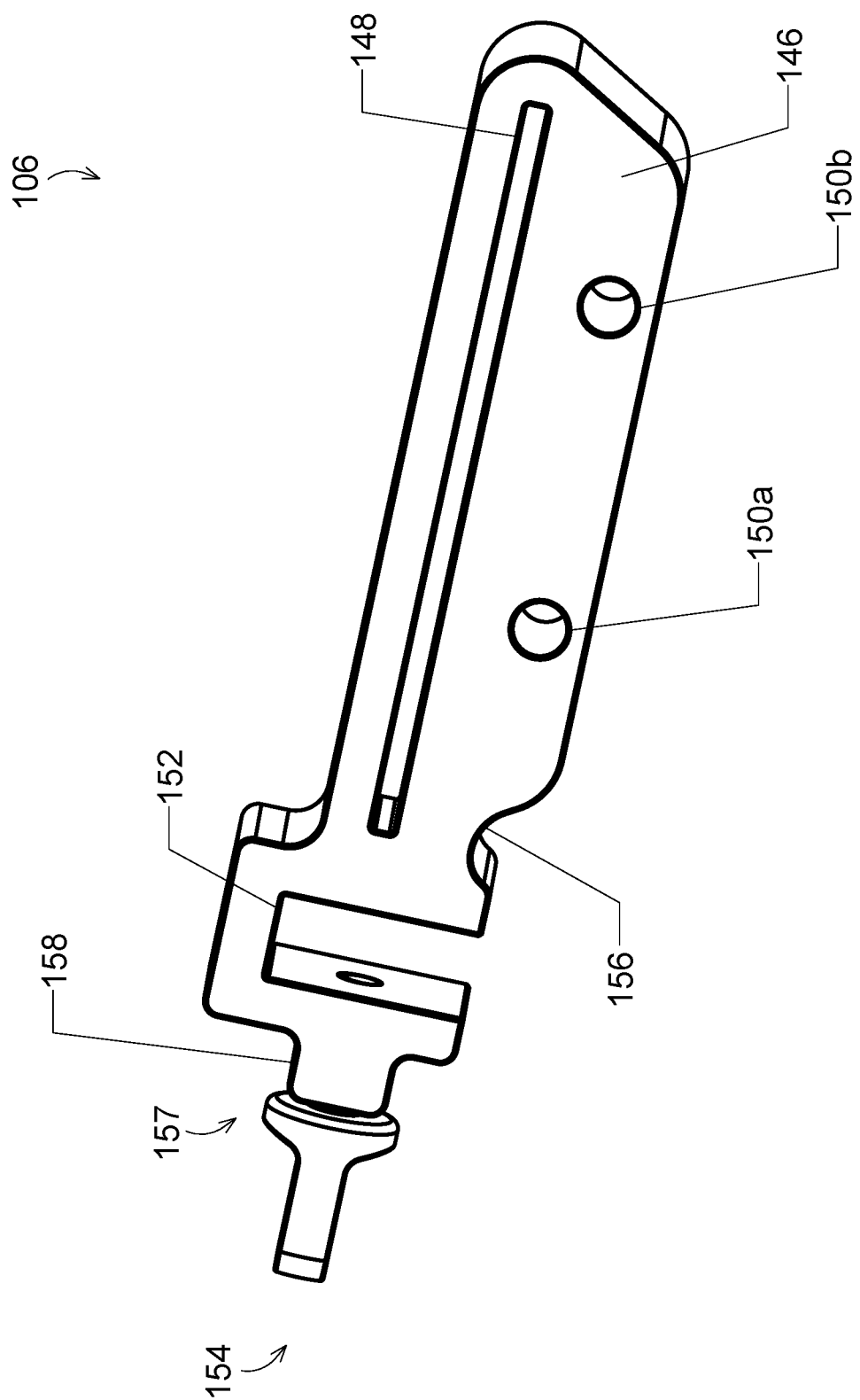
FIG. 6 is a perspective view of a resection guide of the surgical instrumentation system of FIG. 1.
Figure 7:
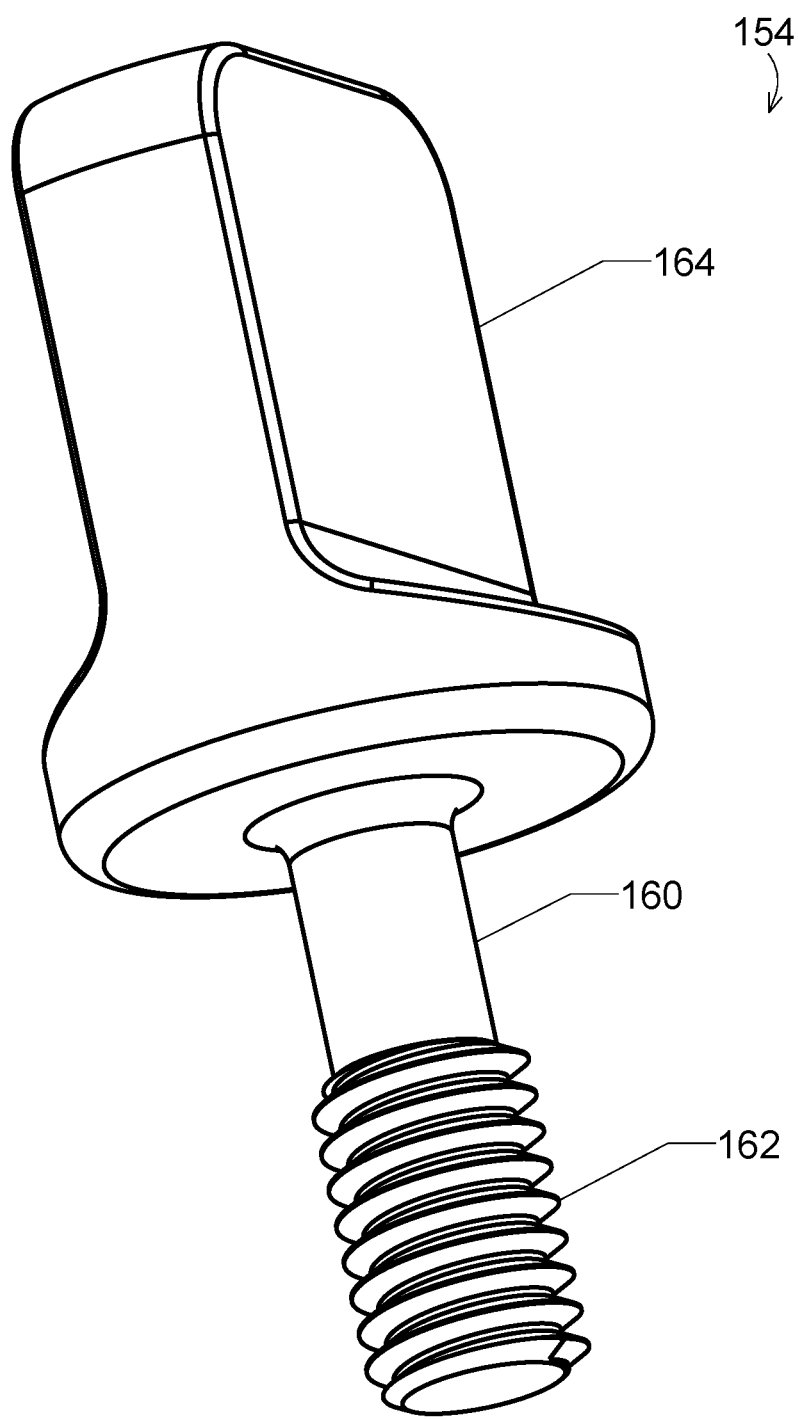
FIG. 7 is a perspective view of a fastener of the resection guide of FIG. 6.

The resection guide 106 is best shown in FIG. 6. The resection guide includes a planar face 146 that includes a guide surface 148 for guiding the cutting tool 110, which in this exemplary embodiment is in the form of a slit-shaped aperture shaped to receive the cutting tool e.g., a captured guide surface, though the guide surface 148 can take multiple forms and configurations, e.g., an open guide surface. The planar face 146 further includes a plurality of through holes 150, sized to receive, for example, optional stabilization pins, studs, rods or screws. Similar to the general shape of the slit-shaped aperture, the planar face 146 has a longer width than height.

A guide aperture 152 is formed through the planar face 146 and is shaped to receive (e.g., matingly receive) or otherwise operatively engage the shaft 116 of the retractor 102, and allow the resection guide to movably engage the shaft in the longitudinal direction 119 of the shaft. A contour or cutout 156 is provided adjacent the guide aperture shaped to receive a thumb to facilitate manual manipulation of the resection guide. The resection guide also includes a fastener 157 e.g., a threaded aperture 158 shaped to receive a thumb screw 154, which allows the resection guide to be fixed into position on the shaft upon fastening. The thumb screw 154 includes a shaft 160 containing threads 162 complimentary to threading provided in threaded aperture 158, and a thumb handle 164.

Operation of the surgical instrumentation system 100 will now be described in detail. Prior to attaching, a surgeon will generally use a humeral template to make a Bovie™ mark on the head that provides a broad template for the cut angle. The curved section 114 is rotated around the humeral head such that the curved section wraps around the posterior aspect of the humeral head 112, keeping it snug to the rotator cuff if present. Owing to the arc 120 provided by the curved section 114, the curved section 114 protects the auxiliary nerve and, as the cutting tool is passed via the guide surface 148 through the humeral head, the retractor prevents the cutting tool 110 from penetrating beyond the humeral head in the posterior, superior and inferior aspects. Since the humeral head resection guide is connected directly to the retractor 102, the retractor is always in a position to correctly limit the travel of the cutting tool 110 and prevent damage to neural and vascular structures and other soft tissue.

The resection guide 106 is properly aligned by aligning the desired forearm alignment shaft to be parallel with the forearm while it is flexed at 90 degrees. As noted, the middle forearm alignment shaft 126b corresponds to 30 degrees of retroversion when aligned with the forearm as shown in FIG. 1. The secondary humerus alignment shaft 136a or 136b, as appropriate, are used as a secondary safeguard for alignment and kept parallel to respective left or right humerus again as shown in FIG. 1.

While keeping the retractor snug to the rotator cuff insertion on the greater tuberosity, the resection guide 106 is positioned next to the humeral head 112 and secured to the shaft 116 by tightening the thumb screw 154. Then two short pins are advanced through the through holes 150a and 150b. This secures the resection guide 106 to the proximal humerus. A cutting tool 110, powered by an oscillating saw 108, is then placed through the slit aperture formed by the cutting guide surface 148 of the resection guide, and used to cut the humeral head. Prior to making the cut, it can be confirmed that the previous Bovie™ mark using the template is at a roughly similar angle to the slot in the cutting guide.

FIGS. 8-13 disclose a surgical instrumentation system 800 for a shoulder arthroplasty according to an alternative embodiment. In this exemplary embodiment, the system 800 includes a retractor 802, an alignment guide 804, and a resection guide 806 to guide a cutting tool to resection a humeral head 812.

Figure 9:
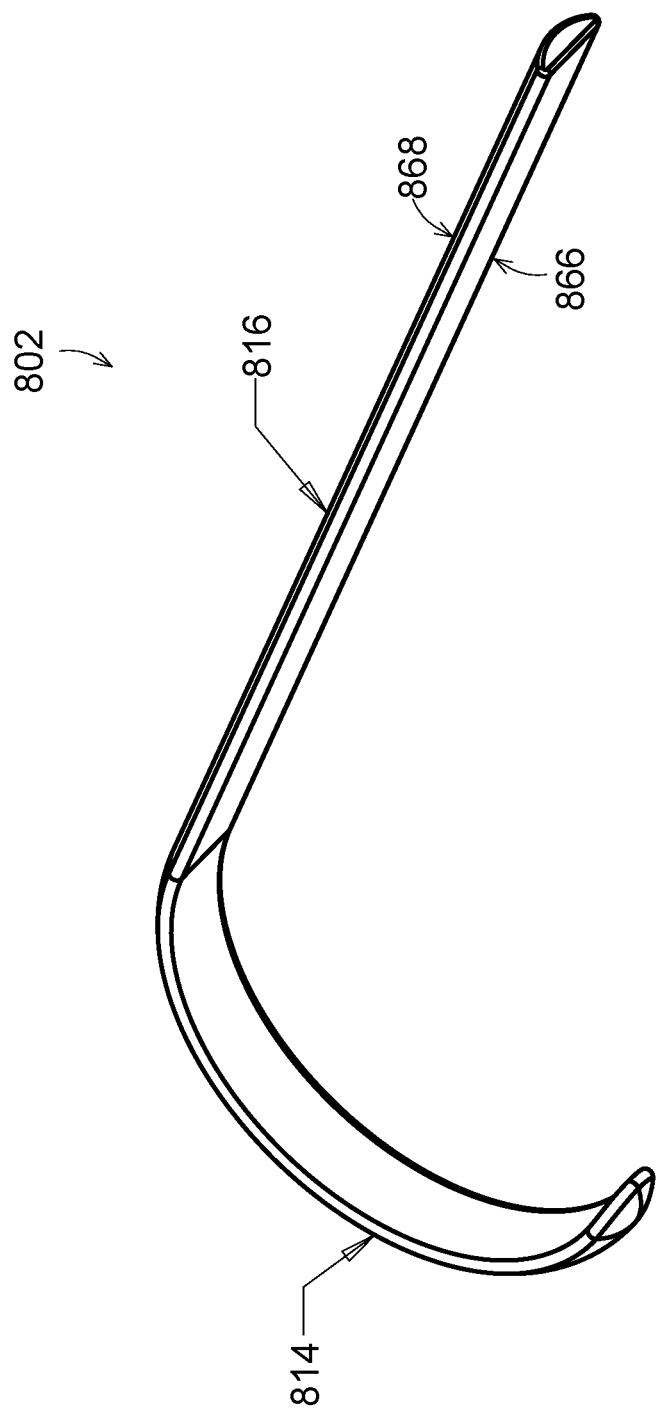
FIG. 9 is a perspective view of a retractor of the surgical instrumentation system of FIG. 8.

With reference to FIG. 9, the retractor 802 includes a curved section or curved end 814, similar to curved section 114 discussed above, that is structured to wrap around and substantially engage a posterior portion of the humeral head 812. A shaft 816 extends from the curved section 814 about its proximal end, having the same cross-sectional shape throughout the entire longitudinal length of the shaft 816. In this exemplary embodiment, the shaft has a planar side 866 and curved side 868 opposite the curved side, defining a substantially "D" shaped longitudinal cross-section.

Figure 10:
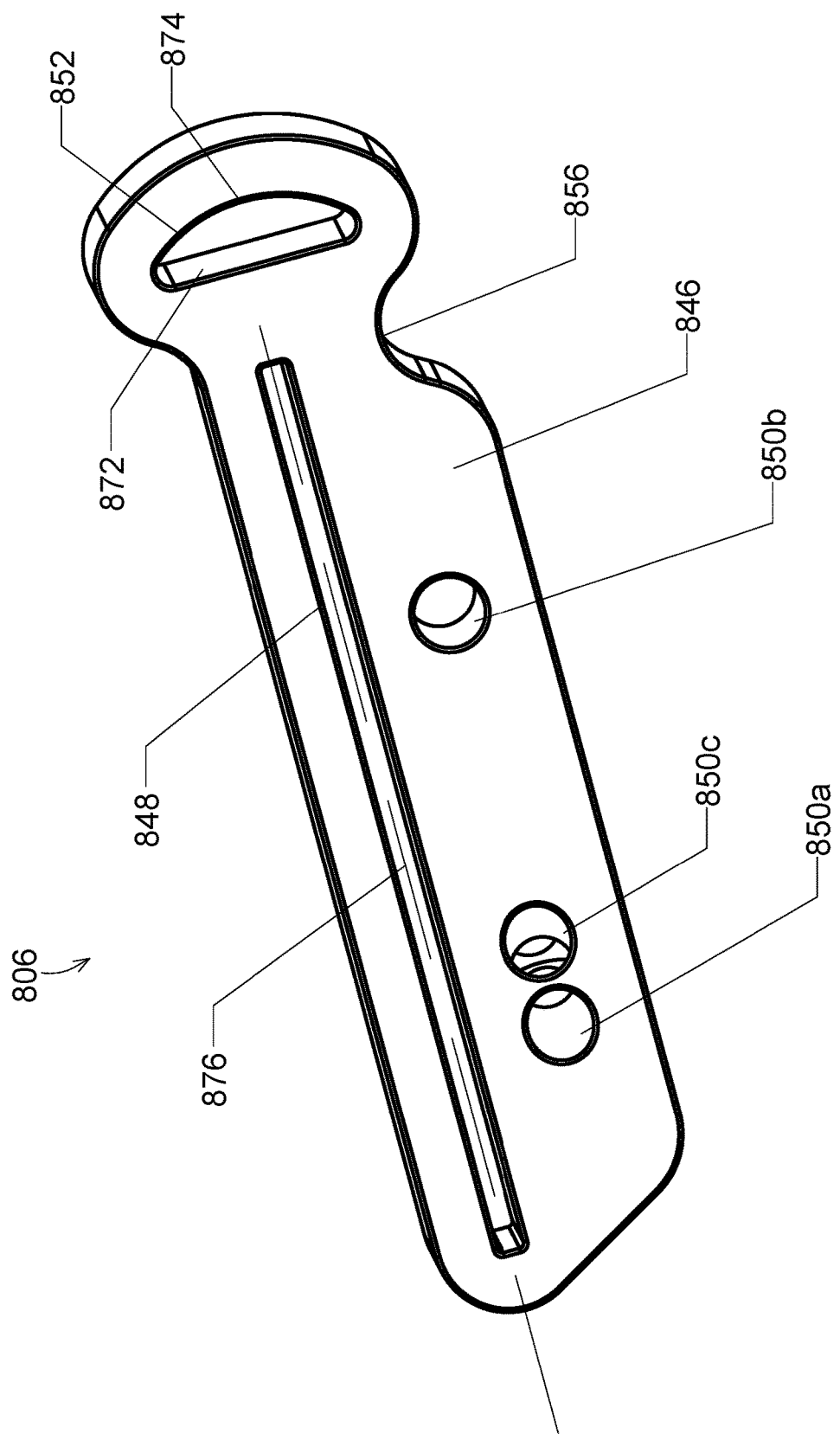
FIG. 10 is a perspective view of a resection guide of the surgical instrumentation system of FIG. 8.

The resection guide 806 is shown best in FIG. 10, and includes a planar face 846, a guide surface 848 for guiding a cutting tool, a plurality of through holes 850a, 850b, 850c and a thumb contour or cutout 856 similar to their counterparts in the resection guide 106, discussed in detail above. In the present exemplify embodiment the guide surface is a captured guide surface, but can alternately be an open-faced (i.e. open) guide surface. The resection guide 806 further includes a guide aperture 852 for matingly receiving the shaft 816 that, in this particular embodiment, is a fully enclosed aperture. The guide aperture 852 includes a planar side 872 and a curved side 874 opposite the planar side. The planar side 872 is substantially perpendicular to a longitudinal axis 876 defined by the guide surface 848.

Figure 11:
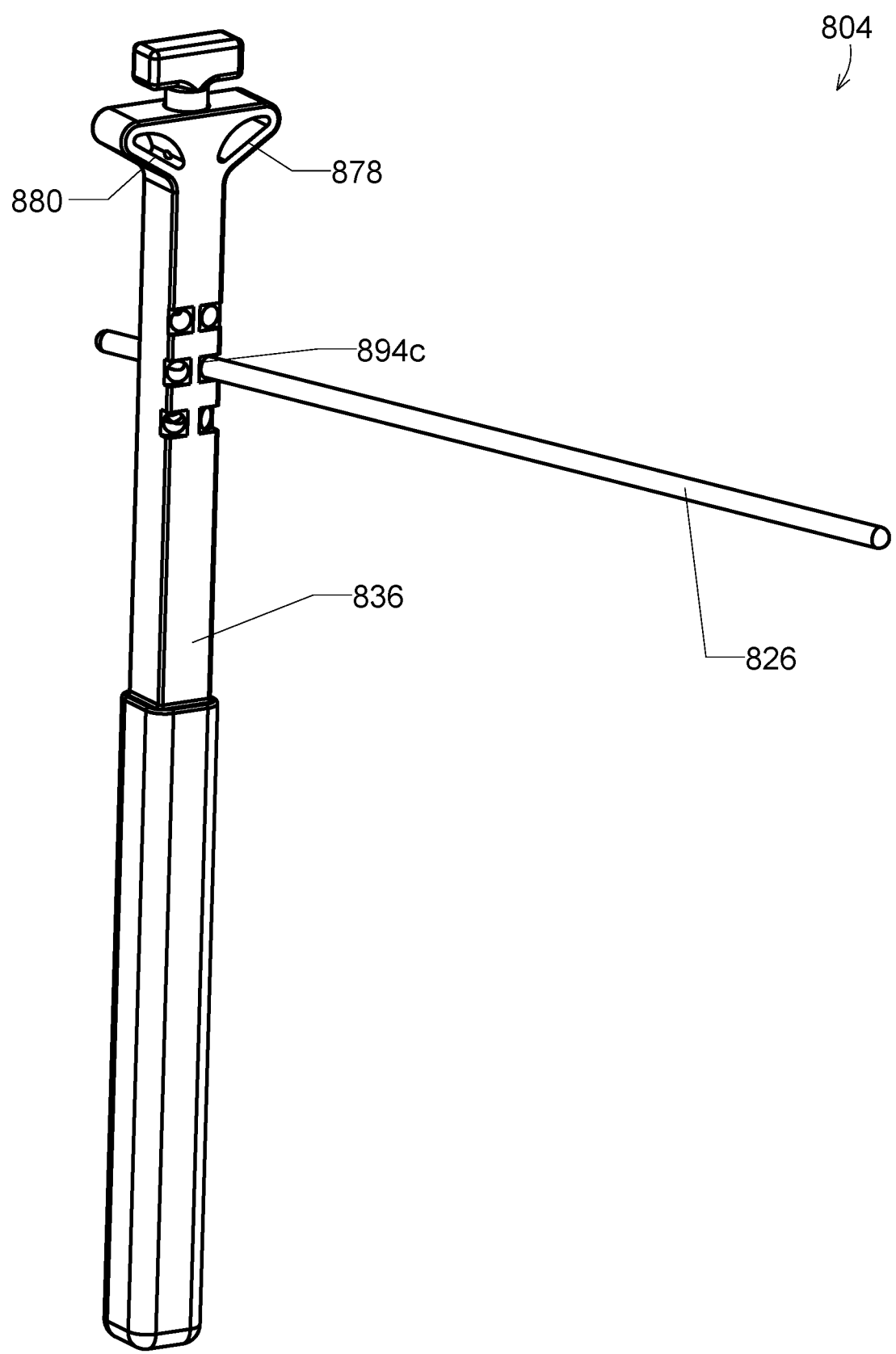
FIG. 11 is a perspective view of an alignment guide of the surgical instrumentation system of FIG. 8.
Figure 12:
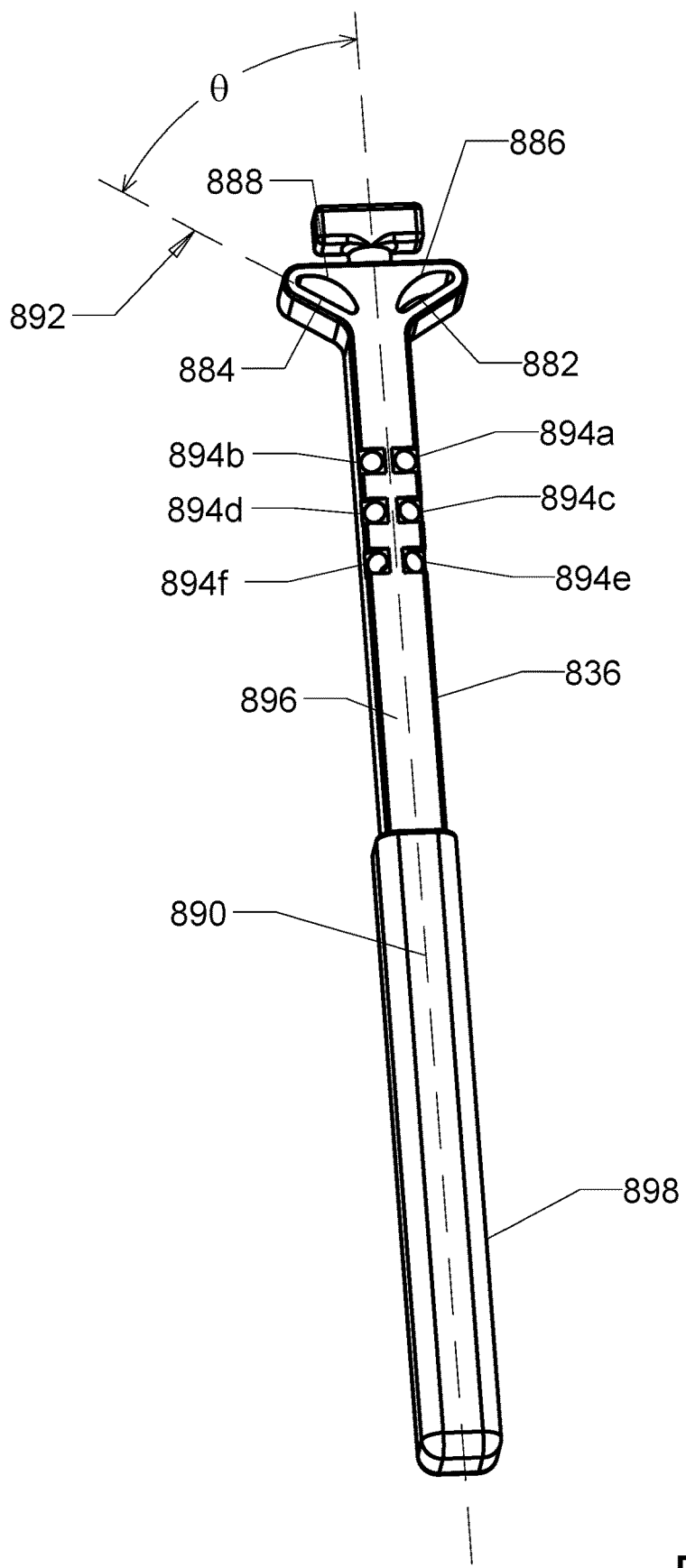
FIG. 12 is a perspective view of a primary alignment shaft of the alignment guide of FIG. 11.
Figure 13:
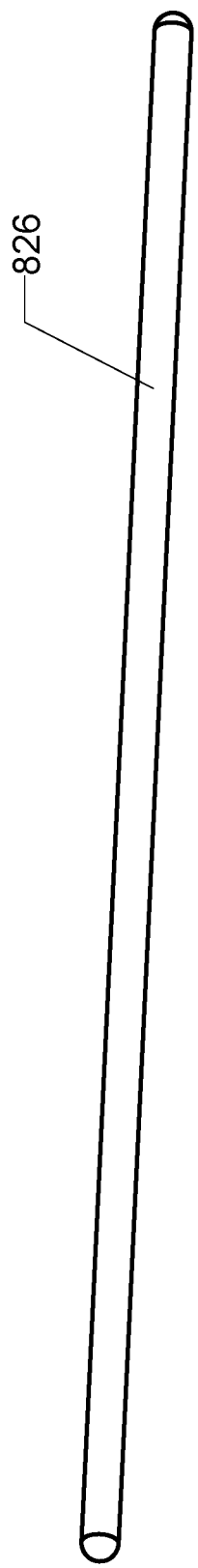
FIG. 13 is a perspective view of a retention rod of the alignment guide of FIG. 11.

The alignment guide 804 is best shown in FIGS. 11-13. The alignment guide includes a (primary) alignment shaft 836 attachable to the shaft 816 extending from the curved section 814 of the retractor 802. The alignment guide 804 is connected to the retractor 802 via a first alignment aperture 878 or a second alignment aperture 880. The alignment apertures 878, 880 are shaped similar to the guide aperture 852 and respectively include a planar side 882, 884 and a curved side 886, 888 opposite the planar side. The alignment shaft 836 defines a longitudinal axis 890 that extends at an angle θ from a plane 892 defined by the planar side 884 that can range, for example, from about 30 degrees to about 75 degrees, including 25, 35, 40, 45, 50, 55, 60, 65 and 75 degrees. The alignment guide further includes planar anterior and posterior faces 896. A distal section 898 of the shaft is provided with a larger diameter or width section to facilitate easier manual manipulation.

Shown best in FIG. 12, the alignment guide includes a plurality of through holes 894 sized and adapted to receive a fixation rod 826. Through holes 894a, 894c and 894e are designated for a left humeral resection and through holes 894b, 894d and 894f are designated for a right humeral resection. Through holes 894a, 894c and 894e are provided at differing angles with respect to the planar face 896 so as to provide different degrees of retroversion, analogous to the different degrees of retroversion provided by the forearm alignment shafts 126a, 126b and 126c, discussed above, when the fixation rod 826 is aligned with the forearm.

For example, through hole 894c is angled, with respect to the planar face 896, such that about 30 degrees of retroversion will be applied when this through hole receives the fixation rod and the fixation rod is aligned with the forearm, as will be discussed in greater detail below. Additional through holes 894, and/or through holes 894 cut at different angles with respect to the plane 896, can be provided to provide additional and/or different degrees of retroversion. Indicia (not shown) can be provided on the alignment shaft similar to indicia 130, discussed above, to indicate the degree of retroversion provided by the particular through hole 894 when used to receive the fixation rod 826.

Figure 8:
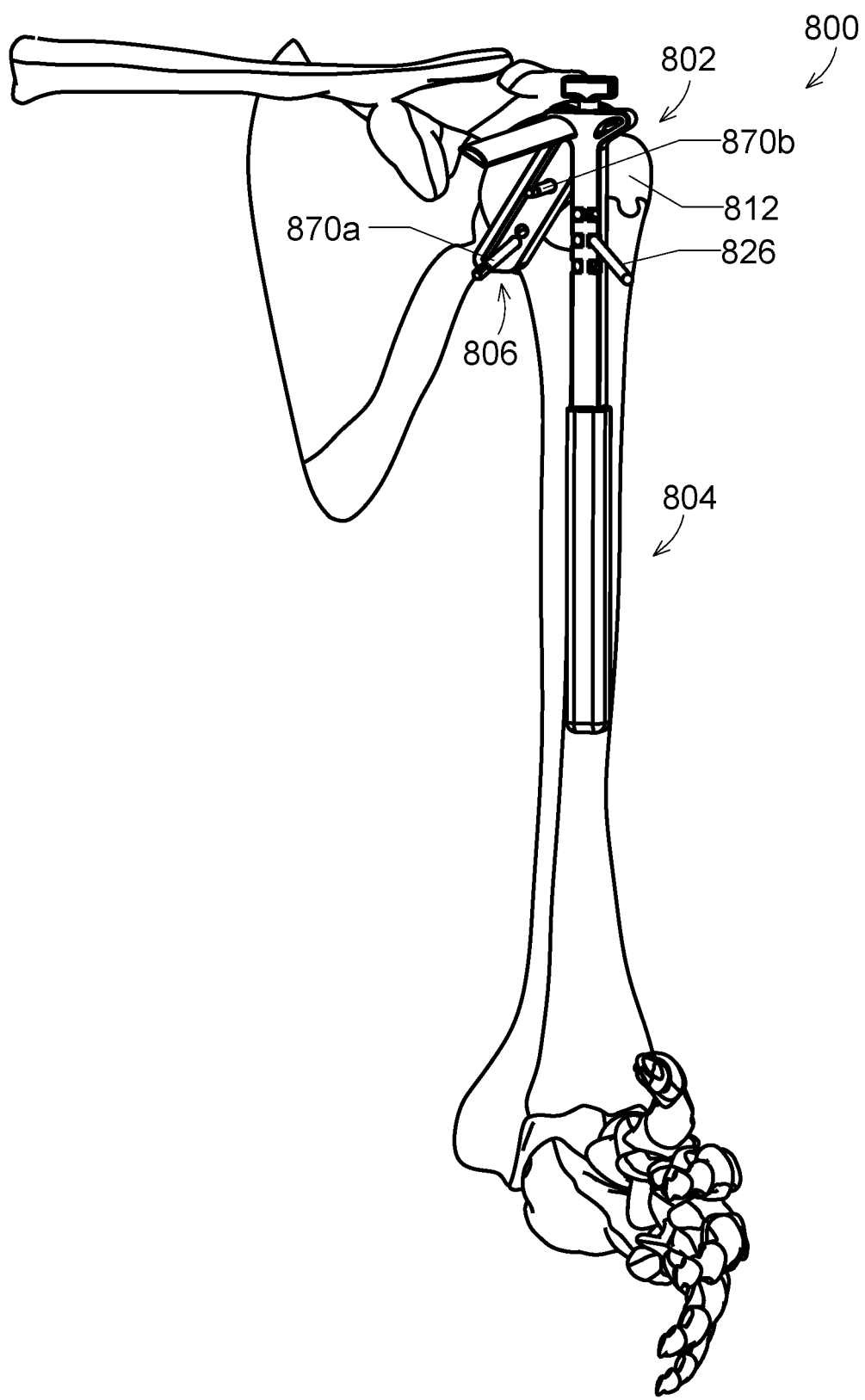
FIG. 8 is a perspective view of a surgical instrumentation system in accordance with an alternative, exemplary embodiment of the subject disclosure.

Operation of the surgical instrumentation system 800 will now be described in greater detail. The curved section 814 is rotated around the humeral head 812 similar to as described above with respect to the surgical instrumentation system 100 and curved section 114. The resection guide 806 is advanced along the shaft 816 until adjacent to the humeral head 812. The alignment shaft 836 is then advanced along the shaft and aligned parallel to the humerus as shown in FIG. 8 to initially position the resection section. To adjust the alignment of the alignment shaft face 836, the fixation rod 826 is then advanced through the appropriate through hole 894 of the alignment shaft corresponding to the desired degree of retroversion for the humeral resection, and aligned with the forearm, again as shown in FIG. 8. The resection guide 806 and cutting guide surface 848 are in their final position, and pins 870a, 870b can be applied through through holes 850a, 850b to further secure the resection guide 806 to the humeral head 812 in this final position. A cutting tool (not shown) can then be guided via the guide cutting surface 848 to resect the humerus.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

The invention claimed is:

1. A surgical instrumentation system for a shoulder arthroplasty comprising:
 a retractor including:
  a curved section structured to wrap around and substantially engage a posterior portion of a humeral head,
  a shaft extending from the curved section, said shaft defines a first plane,
  an alignment guide extending from the retractor, the alignment guide comprising a plurality of primary alignment shafts, each of the primary alignment shafts extends obliquely from a central location of the shaft, and
  an orthogonal segment defining a second plane orthogonal to the first plane and connecting the shaft to a distal end of the alignment guide; and
 a resection guide attachable to the shaft of the retractor and configured for lockable adjustment along the shaft, the resection guide including a guide surface for guiding a cutting tool to resect the humeral head;
 wherein a first of the primary alignment shafts extends at a first angle of about 140 to about 145 degrees, a second of the primary alignment shafts extends at a second angle of about 152 to about 157 degrees, and a third of the primary alignment shafts extends at a third angle of about 165 to about 169 degrees, each with respect to the first plane, and wherein the curved section, the alignment guide, the plurality of primary alignment shafts and the orthogonal segment are of unitary construct.

2. The surgical instrumentation system of claim 1, wherein the curved section comprises a circular arc having a degree of curvature from about 140 to 210 degrees.

3. The surgical instrumentation system of claim 1, wherein the resection guide includes a guide aperture for receiving a shaft of the retractor.

4. The surgical instrumentation system of claim 1, wherein the guide surface is a captured guide surface or an open guide surface.

5. The surgical instrumentation system of claim 1, wherein the plurality of primary alignment shafts extend substantially transverse to a longitudinal axis of the retractor.

6. A surgical instrument for a shoulder arthroplasty comprising:
   a retractor including:
      a curved section structured to wrap around and substantially engage a posterior portion of a humeral head,
      a shaft extending from the curved section defining a first plane,
      an alignment guide extending from the retractor comprising: plurality of forearm alignment shafts, each of the plurality of forearm alignment shafts extending obliquely from a central location of the shaft,
      an orthogonal segment defining a second plane orthogonal to the first plane and connecting the shaft to a distal end of the alignment guide, and
      a plurality humerus alignment shafts extending transversely from a proximal end of the alignment guide; and
   a resection guide attached to the shaft of the retractor, the resection guide including a guide surface for guiding a cutting tool to resect the humeral head;
   wherein a first of the foreman alignment shafts extends at a first angle of about 140 to about 145 degrees, a second of the foreman alignment shafts extends at a second angle of about 152 to about 157 degrees, and a third of the foreman alignment shafts extends at a third angle of about 165 to about 169 degrees, each with respect to the first plane, and
   wherein the curved section, the alignment guide, the plurality of forearm alignment shafts, the orthogonal segment and the plurality of humerus alignment shafts are of unitary construct.

7. The surgical instrumentation system of claim 6, wherein the plurality of humerus alignment shafts comprises a first humerus alignment shaft and a secondary humerus alignment shaft extending transversely from the proximal end of the alignment guide.

8. The surgical instrumentation system of claim 6, wherein the retractor and resection guide are of unitary construction.

* * * * *